US 6,733,576 B2

(12) United States Patent
Nimberger et al.

(10) Patent No.: US 6,733,576 B2
(45) Date of Patent: May 11, 2004

(54) GAS SAMPLING SEPARATOR

(75) Inventors: Spencer M. Nimberger, Houston, TX (US); Kevin J. Cessac, Houston, TX (US)

(73) Assignee: PGI International, Ltd., Houston, TX (US)

( * ) Notice: Subject to any disclaimer, the term of this patent is extended or adjusted under 35 U.S.C. 154(b) by 99 days.

(21) Appl. No.: 09/951,602

(22) Filed: Sep. 13, 2001

(65) Prior Publication Data

US 2002/0092425 A1 Jul. 18, 2002

Related U.S. Application Data

(60) Provisional application No. 60/234,003, filed on Sep. 20, 2000.

(51) Int. Cl.[7] .......................... B01D 45/00; B01D 45/14; G01N 1/00
(52) U.S. Cl. .......................... 96/413; 55/428; 55/428.1; 55/434.4; 55/447; 55/450; 55/458; 55/461; 73/28.04; 73/863.12; 73/863.21; 73/863.22; 73/863.24; 73/863.81; 73/31.07; 422/101
(58) Field of Search .................... 55/385.1, 428, 55/428.1, 433, 434.4, 447, 448, 450, 458, 459.1, 461, DIG. 34; 96/413, 243, 417; 73/19.12, 28.04, 28.05, 31.07, 863.11, 863.12, 863.21, 863.22, 863.23, 863.24, 863.25, 863.81, 864.73; 422/101

(56) References Cited

U.S. PATENT DOCUMENTS

| | | | | | |
|---|---|---|---|---|---|
| 2,987,921 | A | * | 6/1961 | Kraftson | 73/863.12 |
| 3,070,990 | A | * | 1/1963 | Krinov | 73/863.12 |
| 4,014,216 | A | * | 3/1977 | Thornton et al. | 73/863.23 |
| 4,144,759 | A | * | 3/1979 | Slowik | 73/863.21 |
| 4,155,247 | A | * | 5/1979 | Kaczmarek et al. | 73/863.21 |
| 4,262,533 | A | * | 4/1981 | Jaeger | 73/863.11 |
| 4,974,455 | A | * | 12/1990 | McGowan et al. | 73/863.12 |
| 5,131,260 | A | * | 7/1992 | Brand et al. | 73/31.07 |
| 5,355,719 | A | * | 10/1994 | Kohsaka et al. | 73/863.21 |
| 6,022,510 | A | * | 2/2000 | Springmann | 73/863.12 |
| 6,289,752 | B1 | * | 9/2001 | Nimberger et al. | 73/863.11 |
| 6,357,304 | B1 | * | 3/2002 | Mayeaux | 73/863.23 |
| 6,444,001 | B1 | * | 9/2002 | Sheffield | 73/863.21 |

* cited by examiner

Primary Examiner—Duane Smith
Assistant Examiner—Jason M. Greene
(74) Attorney, Agent, or Firm—Loren Helmreich; Browning Bushman, P.C.

(57) ABSTRACT

A gas sampling separator 29 for the separation of liquid or other contaminants from gas received from a pipeline may be easily inspected visually and cleaned. A cylindrical body 62 forming a separation chamber 64 is threaded onto a base 40. A tube 68 within the separation chamber receives gas from a port in the base and directs the gas into the separation chamber for separation of the gas from the contaminants. The separated contaminants collect in a sump 58 formed by the base and may be vented upon actuation of a manually actuated valve 76.

19 Claims, 2 Drawing Sheets

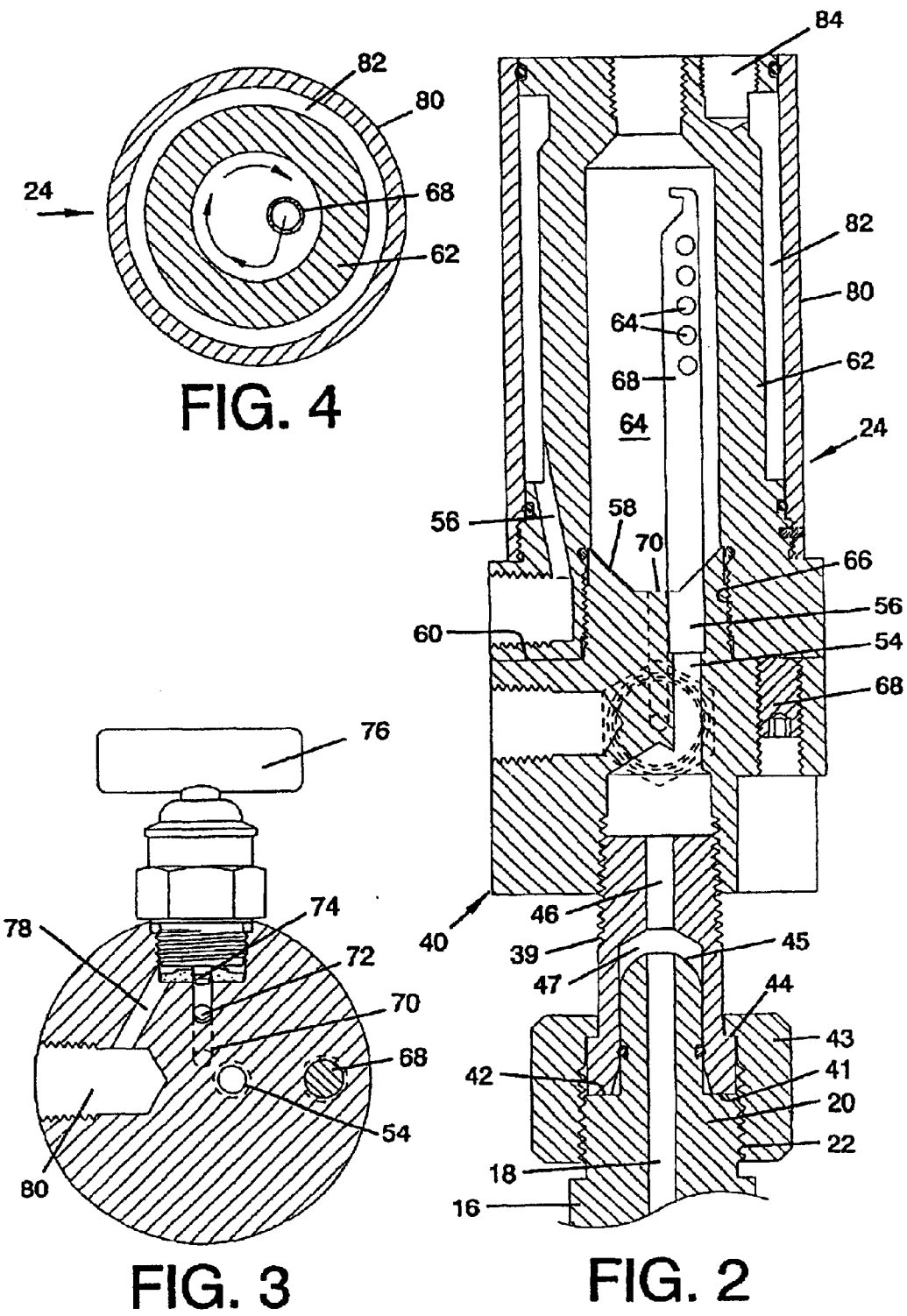

GAS SAMPLING SEPARATOR

REFERENCE TO RELATED APPLICATION

This application claims the benefit of application Serial No. 60/234,003 filed Sep. 20, 2000.

FIELD OF THE INVENTION

The present invention relates to gas sampling separators and, more particularly, to a gas sampling separator that may be easily inspected and cleaned between uses to minimize or prevent contamination of the sampled gas.

BACKGROUND OF THE INVENTION

Gas sampling separators remove liquids, solids and other contaminants from gas received from a gas supply, such as a gas pipeline. Separators are typically fabricated from a unitary sample bottle which has a port welded into the side of the bottle about a third down from the bottle top. The contaminated gas stream from the pipeline passes through the side port, and the liquid or other contaminant is allowed to drop out into the separator lower cavity while the gas exits the top port of the separator. A lower port from the bottle is valved and used to periodically drain the separator of liquid or other contaminants.

A significant problem with conventionally designed separators is that they cannot be inspected for contamination and/or easily cleaned between uses to minimize or prevent contamination of the sampled gas, and to prevent cross contamination of gas samples. Furthermore, the conventional design of a gas sampling separator lends itself only to relatively inefficient heating with electric or water trace lines.

SUMMARY OF THE INVENTION

The present invention is directed to a gas sampling separator for the removal of liquid and other contaminant from gas received from a gas pipeline. The gas sampling separator is conveniently mounted on a probe extending into the pipeline and may be easily inspected to determine the amount of liquid and/or foreign matter removed from the gas and then easily cleaned. The separator has a lower removable base with a bore to receive gas from a pipeline and an upper generally cylindrical body forming a separation chamber. A tube communicating with the bore may be mounted in the separation chamber within a cylindrical body, and has lateral openings for gas exiting the tube into the separation chamber in a swirling action. The cylindrical body of the separator is removably connected to the base. The upper end of the base forms a sump for the separated liquid and may be easily inspected visually upon removal of the cylindrical body from the base.

It is frequently desirable to heat the separator so that the surfaces contacting the gas are not at a temperature below the hydrocarbon dew point of the gas being sampled. For this purpose, an outer water jacket or sleeve may be mounted about the cylindrical body to form an annular heating chamber for receiving hot water or hot gas for heating of the separator. The water jacket is easily removed with the cylindrical body and the integrity of the water jacket is not affected by disassembly of the cylindrical body.

It is an object of this invention to provide a gas sampling separator which permits an easy inspection to determine the amount of liquid and/or foreign matter being separated from the gas.

A further object of the invention is the provision of a gas suppling separator which may be easily cleaned between uses of the separator.

It is a feature of the invention to provide such a gas sampling separator having fluid contacting surfaces for heating to a temperature above the hydrocarbon dew point of the gas being sampled. The separator preferably includes an annular jacket to receive a heated fluid for heating the gas within the separation chamber.

These and further objects, features, and advantages of the invention will be apparent from the following specification, wherein reference is made to the figures in the accompanying drawings.

BRIEF DESCRIPTION OF THE DRAWINGS

FIG. 2 is an enlarged sectional view of the gas sampling separator shown in 15; FIG. 1.

FIG. 3 is an enlarged sectional view taken generally along line 3—3 of FIG. 1.

FIG. 4 is an enlarged sectional view taken generally along line 4—4 of FIG. 1.

DESCRIPTION OF THE PREFERRED EMBODIMENTS

Figure 1:
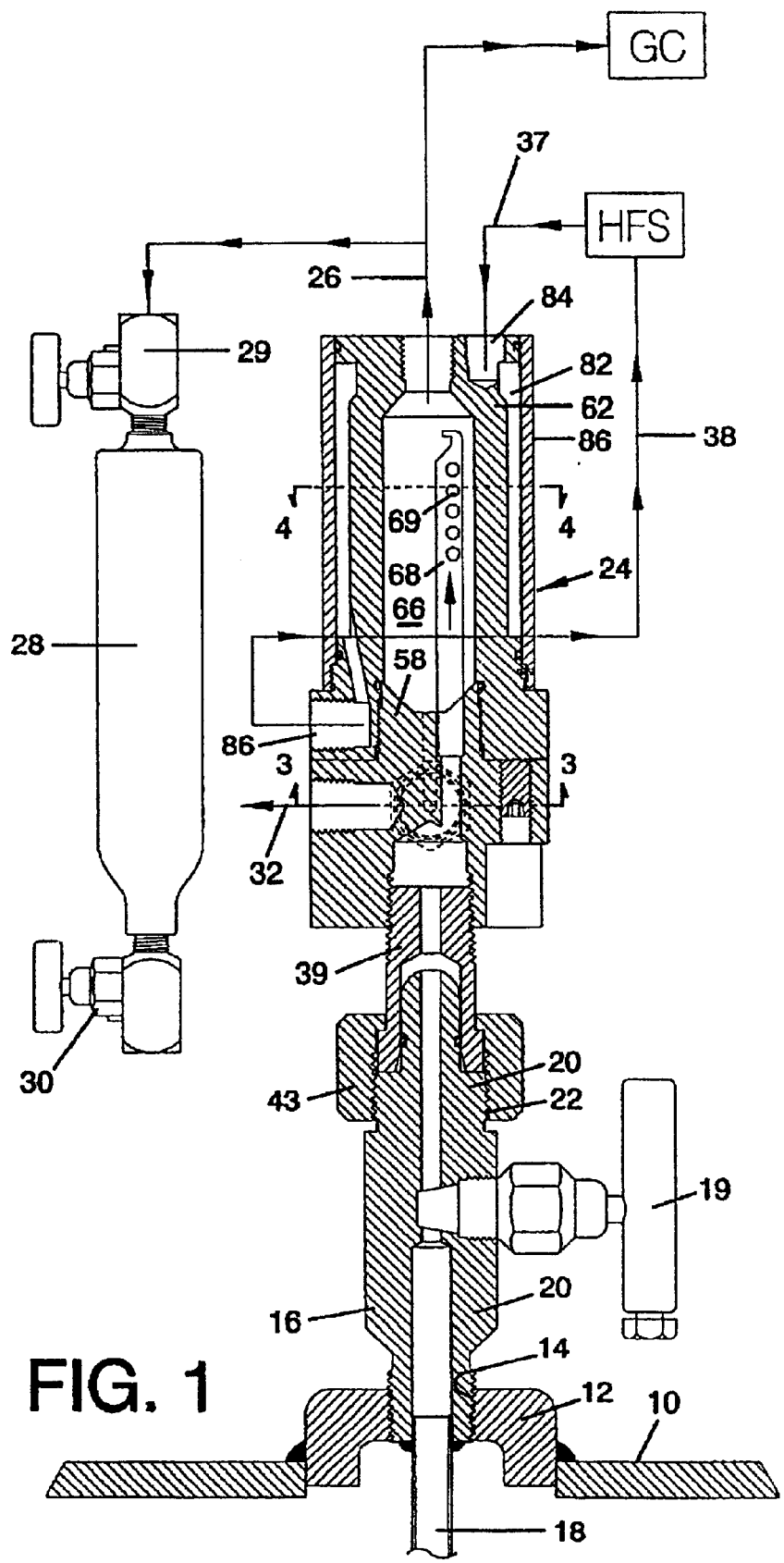
FIG. 1 is a generally schematic view of a gas sampling system to obtain gas samples from gas passing through a pipeline with the gas sampling separator mounted on a probe extending within the pipeline.

Referring now to the drawings and more particularly to FIG. 1, a gas sampling system is illustrated in which the gas sampling separator of the present invention is utilized. The gas pipeline 10 contains fluid gas which is to be sampled. The sampled gas conventionally includes various grades of hydrocarbons, and the BTU content of the sampled gas is used to determine the value of the gas passing through the pipeline. A weld flange has internally threaded opening 14 therein and a probe 16 is mounted within internally threaded opening 14. Probe 16 has a bore 18 to receive gas from pipeline 10 and has an upper section 20 which is externally threaded at 22. A manually operated shutoff valve 19 is mounted on probe 16 to control the gas flow from pipeline 10.

The gas sampling separator comprising the present invention is shown generally at 24 and is mounted on upper section 20 of probe 16 to receive gas to be sampled, as will be explained further. Clean gas from gas sampling separator 24 is supplied by line 26 to a gas chromatograph GC or to a sample bottle 28 for the collection of clean gas. Inlet valve 29 is closed off to permit removal of the sample bottle from the system. A valve 30 may be manually operated for obtaining a gas sample of clean gas from bottle 28.

A discharge line 32 from gas sampling separator 24 permits the discharge of separated liquid or foreign matter to the atmosphere or into a collecting chamber. To provide heat for heating of gas sampling separator 24, a hot fluid source shown at HFS for hot water is provided for the supply of hot water through line 37 to gas sampling separator 24. The spent water from separator 24 may be returned by line 38 to hot fluid source HFC, or may be discharged to a dump site. The hot fluid source HFC may comprise hot water obtained from a vehicle, such as a truck.

Referring now also to FIGS. 2 and 3, gas sampling separator 24 has a lower base 40 threaded onto a connector 39 between base 40 and probe 16. Connector 39 has a lower annular end 41 abutting a shoulder 42 on probe 16. Internally threaded nut 43 engages an outer shoulder 44 and threads 22 for tightly connecting connector 39 onto probe 16. Probe 16 has an upper rounded end 45 received within an enlarged lower bore portion 47 of connector 39 for facilitating mounting of connector 39 thereon in axial relation with bore 46 in connector 39 aligned with bore 18 in probe 16.

Base 40 has an axial bore 54 in fluid communication with bore 18 of probe 16. Base 40 has an upwardly extending externally threaded end portion 56 defining a pocket or sump 58 and an annular shoulder 60. An upper cylindrical body 62 has a central bore defining a separation chamber 64. Cylindrical body 62 has an internally threaded end opening 66 for threading of cylindrical body 62 onto upper end portion 56. A set screw 68 rotationally secures cylindrical body 62 onto upper portion 56. A gas discharge tube 68 is mounted within bore 54 on base 40 and extends upwardly within separation chamber 64. The upper end of tube 68 is closed and lateral openings 69 in tube 68 permit the discharge of gas laterally within separation chamber 64 to provide a swirling action or vortex for the gas entering separation chamber 64. Liquid and foreign matter drop downwardly into sump 58 and the gas moves upwardly for discharge from line 26.

Base 40 has a port 70 at the bottom of sump 58 in fluid communication with port 72 which is blocked by plug 74 at an end of manually actuated valve 76. Upon opening of valve 76 and unseating of plug 74, liquid in sump 58 is passed by port 78 to port 80 and then to discharge line 32 for venting or flow to a collection chamber. Actuation of valve 76 permits the venting of the liquid and any foreign matter to atmosphere or to a suitable collection member.

It is desirable that separator 24 be heated under ambient conditions in which separator 24 has a temperature below the hydrocarbon dew point of the gas being sampled. For this purpose, an outer fluid jacket 80 is mounted about cylindrical body 62 and forms an annulus 82 therebetween. Hot fluid such as water from hot fluid source HFC is provided through port 84 to annulus 82. The spent water is discharged through port 86 and discharge line 38 for return to the heat source. The heat source may comprise heated water or heated gas. In many instances, hot water from a vehicle such as a truck may be utilized with suitable hoses connected to separator 24. Water jacket 80 is particularly effective for heating separation chamber 64.

The separator 24 is particularly adapted for inspection and subsequent cleaning. For inspection, body 62 including water jacket 80 may be unthreaded from externally threaded end portion 56 of base 40 upon a release of set screw 68. With body 62 removed, sump 58 and bore 70 may be easily viewed for determining the amount of liquid and/or foreign matter therein. Pressurized air may be utilized for cleaning. Likewise, bore 46 in connector 39 may be cleaned by removal of separator 24 from connector 39. Upon removal of cylindrical body 62, water jacket 80 remains in position on cylindrical body 62 and the integrity of the water jacket 80 is maintained. After cleaning, cylindrical body 62 may be easily threaded onto base 40 for assembly.

From the above, it is apparent that gas sampling separator 24 is designed for inspection and cleaning by a simple removal of cylindrical body 62 from base 40. Further, water jacket 80 provided for heating of separator 24 is connected to cylindrical body 62 and removable with cylindrical body 62. Separator 62 may be easily disassembled after each use for inspection and/or cleaning.

In an alternative embodiment, cylindrical body 62 could have external grooves or fins on the OD for better heat transfer from the heated fluid. Tube 68 could be bent in an inverted J-shape, or could have inverted L-shape configuration so that fluid would impact a side wall at the body 62, either directly or at an angle. Cavity 82 could be formed in the body of the separator, so that fluid was channeled through drilled ports in the body.

While a preferred embodiment of the present invention has been illustrated in detail, it is apparent that modifications and adaptations of the preferred embodiment will occur to those skilled in the art. However, it is to be expressly understood that such modifications and adaptations are within the spirit and scope of the present invention as set forth in the following claims.

What is claimed is:

1. A gas sampling separator for the separation of contaminants from gas received from a probe extending within a pipeline, said gas sampling separator comprising:

a base for connection to said probe and having a port for communicating with a gas supply port in said probe to receive contaminated gas;

a body removably mounted on said base and defining an upper gas separation chamber to receive gas from said base, said body having a gas discharge port adjacent an upper end of said separation chamber for the discharge of cleaned gas from said chamber, said body being removable from and reconnectable to said base for inspection and cleaning; and said base having a sump in an upper portion of said base for receiving contaminants adjacent a bottom of said separation chamber and a contaminant discharge port from said sump for the selective discharge of contaminants from said sump.

2. The gas sampling separator as defined in claim 1, further comprising:

an upwardly extending tube mounted within said separation chamber and in fluid communication with said port in said base for the discharge of gas into said separation chamber.

3. The gas sampling separator as defined in claim 2, wherein said tube has a plurality of lateral openings therein for the discharge of gas into said separation chamber in a generally lateral direction.

4. The gas sampling separator as defined in claim 1, further comprising:

a fluid jacket sleeve extending about and mounted on said body to define a heating annulus between said body and said sleeve for receiving hot fluid for heating said body.

5. The gas sampling separator as defined in claim 4, further comprising:

a hot fluid entrance port to said heating annulus for communicating with a hot fluid source; and an exit port for discharging spent hot fluid from said heating annulus.

6. The gas sampling separator as defined in claim 5, wherein said entrance and said exit ports are mounted on said body and removed with said body from said base upon disassembly of said body from said base.

7. The gas sampling separator as defined in claim 1, wherein said contaminant discharge port for said sump is visually exposed for observation upon the disassembly of said body from said base.

8. The gas sampling separator as defined in claim 1, further comprising:

a connector between said probe and said base, said connector having an enlarged lower bore portion for receiving an upper end of said probe to facilitate alignment of said connector with said probe.

9. A gas sampling separator for the separation of contaminants from gas received from a probe extending within a gas pipeline, the separator comprising:

a base for mounting on the probe and having a bore for fluid communication with a bore in the probe to receive contaminated gas from the pipeline;

a body removably mounted on said base and defining a gas separation chamber;

a tubular member extending upwardly within said chamber in fluid communication with said bore in said base to receive gas therefrom and to discharge gas within said gas separation chamber for the separation of contaminants from the gas;

said body having a gas discharge port in an upper portion of said body;

a fluid jacket sleeve extending about and mounted on said body to define a heating annulus between said body and said sleeve for receiving hot fluid for heating said body; and said base having a sump for receiving contaminants adjacent a bottom of said chamber and a contaminant discharge port from said sump for the selective discharge of contaminants from said sump.

10. The gas sampling separator as defined in claim 9, wherein said tube has a plurality of lateral openings thereon for discharge of gas into said separation chamber in a generally lateral direction.

11. The gas sampling separator as defined in claim 9, further comprising:

a hot fluid entrance port to said annulus for communicating with a hot fluid source; and an exit port for discharging spent hot fluid in from said annulus, said entrance and exit ports being in said body and removed with said body upon disassembly of said body from said base.

12. The gas sampling separator as defined in claim 9, wherein said base is removably mounted on said probe.

13. A gas sampling separator for the separation of contaminants from gas received from a probe extending within a gas pipeline, said gas sampling separator comprising:

a base for mounting on the probe and having a bore for fluid communication with a bore in the probe to receive contaminated gas from the pipeline;

an upper body removably mounted on said base and having a gas separation chamber therein;

a fluid passageway extending about said body for receiving hot fluid for heating said body; and a liquid sump adjacent a bottom of said separation chamber, and a liquid discharge port from said sump for the selective discharge of liquid from said sump, said sump being visually exposed upon the disassembly of said body from said base.

14. The gas sampling separator as defined in claim 13, further comprising:

a tube extending upwardly within said separation chamber in fluid communication with said bore in said base to receive gas therefrom and discharge the gas into an upper portion of said separation chamber.

15. The gas sampling separator as defined in claim 13, further comprising:

a connector between said probe and said base removably connected to said probe and to said base, said connector having a bore receiving an upper end of said probe to facilitate alignment of said connector with said probe.

16. The gas sampling separator as defined in claim 13, wherein said body has a generally cylindrical configuration.

17. The gas-sampling separator as defined in claim 13, further comprising:

said fluid passageway formed by a fluid jacket sleeve to define a heating annulus between said body and said sleeve;

a hot fluid entrance port to said heating annulus for communicating with a hot fluid source; and an exit port for discharging spent hot fluid in from said heater annulus.

18. The gas sampling separator as defined in claim 17, wherein said entrance and said exit ports are mounted on said body and removed with said body from said base upon disassembly of said body from said base.

19. The gas-sampling separator as defined in claim 13, further comprising:

a liquid discharge passageway from said sump to discharge contaminants from said sump; and a valve along the passageway for selectively opening to discharge contaminants from the separator.

* * * * *